United States Patent [19]

Ligotti

[11] 4,385,891
[45] May 31, 1983

[54] DENTAL APPARATUS FOR PREVENTING LOSS OF PRECIOUS METAL PARTICLES

[76] Inventor: Eugene F. Ligotti, 7 Bay Hills Ct., Huntington, N.Y. 11743

[21] Appl. No.: 252,697

[22] Filed: Apr. 9, 1981

[51] Int. Cl.³ .................................................. A61C 17/04
[52] U.S. Cl. ..................................... 433/92; 210/311; 210/249
[58] Field of Search .................. 433/92; 128/276, 278; 210/311, 247, 251, 249, 250, 477, 444, 443, 454

[56] References Cited

U.S. PATENT DOCUMENTS

| | | | |
|---|---|---|---|
| 995,402 | 6/1911 | Davis | 210/311 |
| 1,361,243 | 12/1920 | Fusom | 210/443 |
| 2,905,418 | 9/1959 | Escartin | 210/249 |
| 3,012,323 | 12/1961 | Thompson | 433/92 |
| 3,043,432 | 7/1962 | Megesi | 210/311 |
| 3,482,313 | 12/1969 | Stram | 433/92 |
| 4,273,126 | 6/1981 | Grane et al. | 433/92 |
| 4,328,101 | 5/1982 | Borden | 433/92 |
| 4,332,560 | 6/1982 | Rait | 433/92 |

Primary Examiner—Gene Mancene
Assistant Examiner—John J. Wilson
Attorney, Agent, or Firm—Beveridge, DeGrandi & Kline

[57] ABSTRACT

Particles of precious metal are recovered from a mixture drawn from the mouth of a dental patient. An enclosure is interiorly divided by a perforated baffle into an upper chamber and a lower chamber. The mixture is introduced into the lower chamber by an inlet conduit which has a substantially smaller cross section than the lower chamber so that a reduced velocity in the lower chamber will permit gravitational settlement of the particles. Residual fluids flow upwardly through the perforated baffle at a relatively low velocity, and they are removed through an outlet conduit which extends into the upper chamber and is connected to a vacuum source.

11 Claims, 4 Drawing Figures

DENTAL APPARATUS FOR PREVENTING LOSS OF PRECIOUS METAL PARTICLES

BACKGROUND OF THE INVENTION

This invention relates to dental apparatus for separating particles of precious metals from a mixture of debris, air and water drawn from the mouth of a dental patient.

Precious metals such as silver and gold are commonly used by dentists for filling cavities in teeth. Inevitably, during the cavity-filling procedure, scraps of these precious metals fall into the patient's mouth. Also, where it is necessary to drill in existing precious metal fillings, the particles of metal produced by drilling fall into the patient's mouth.

During operative procedures which involve the drilling and filling of teeth, it is customary to use a saliva ejector, a central suction unit and a dental spittoon. The saliva ejector is operated continuously to aspirate saliva from the patient's mouth, and the dental spittoon is used after the patient rinses his mouth with water at the conclusion of the procedure. Most metal scaps and other debris are removed by the central suction unit which is used intermittently by the dental assistant. Such a suction unit includes a short rigid suction tip which is inserted and manipulated in the mouth to the areas where debris has accumulated, a suction hose which is connected telescopically to the suction tip, a trapping device which filters debris from the materials in the hose, and a suction pump which creates a subatmospheric pressure to draw a mixture of air, water and debris from the patient's mouth into the suction tip and through the hose.

The composition of the debris collected in the trapping devices of central suction units will vary according to the use of the unit. The debris from operative procedures includes precious metals, ground tooth structure, ground cements, food particles and pieces of root sections. Oral surgery yields blood, gingivel tissue, suture clippings, pieces of bone, pus and other infection fluids. Prophylaxis yields calculus and cleaning materials. All of the above items are mixed with saliva, and all are caught by the known trapping devices of the central suction units. Customarily, such debris is simply discarded because doctors and their assistants are reluctant to remove the precious metal particles from the unpleasant collection of debris.

The present invention, in the interest of conservation and economy, prevents the loss of particles of precious metals by removing them from the debris drawn from the patient's mouth into the suction tip. The residual debris, i.e. normal debris without the precious metal particles, is eventually received and retained by the trapping device for eventual disposal.

SUMMARY OF THE INVENTION

According to the present invention, a device for separating precious metal particles from a mixture drawn from the mouth of a dental patient includes an enclosure, a baffle located in the enclosure for dividing it into an upper chamber and a lower chamber, an inlet conduit which introduces the mixture into the lower chamber, and one or more openings which extend through the plane of the baffle to enable fluids to flow from the lower chamber to the upper chamber. The inlet conduit has a substantially smaller cross section than the lower chamber, causing the mixture in the lower chamber to have a lower velocity, thereby permitting gravitational settlement of the precious metal particles in the lower chamber. Fluids are able to flow upwardly through the baffle openings which collectively have a greater cross sectional area than the inlet conduit. Due to this dimensional relationship, fluids flowing into the upper chamber from the lower chamber will have a lower velocity than the mixture which flows through the inlet conduit into the lower chamber. An outlet conduit communicates with the upper chamber and receives fluids which enter the upper chamber after the gravitational settlement has occurred. Means are provided for removing from the apparatus at least a lower portion of the enclosure which contains the precious metal particles.

Preferably, the device is constructed so that it may be placed between the suction tip and the suction hose of a conventional central suction system. This is made possible by providing the inlet conduit with an outer end portion which has an outside diameter substantially equal to the inside diameter of the outer end portion of the outlet conduit. A suction tip may be telescopically fitted over the outer end portion of the inlet conduit, and a suction hose may be telescopically received in the outer end portion of the outlet conduit. Preferably, the enclosure includes a closure to which the inlet conduit and outlet conduit are affixed; and, a plurality of openings are provided in the baffle.

It is also preferred that the enclosure includes a removable canister which forms the lower chamber. The apparatus is included in a kit which also has a drainage stand for supporting the canister in an inverted position when the canister is removed from the baffle and conduit.

It is further preferred to have the inlet conduit oriented where it introduces its contents axially into one side of the lower chamber and, at the opposite side of the chamber, to provide the baffle with an imperforate area which prevents the mixture and particles from flowing prematurely into the upper chamber before gravitational settlement has occurred.

Although the invention may take a wide variety of forms, one preferred embodiment thereof is disclosed in the following text and is illustrated in the accompanying drawings.

DETAILED DESCRIPTION

Figure 1:
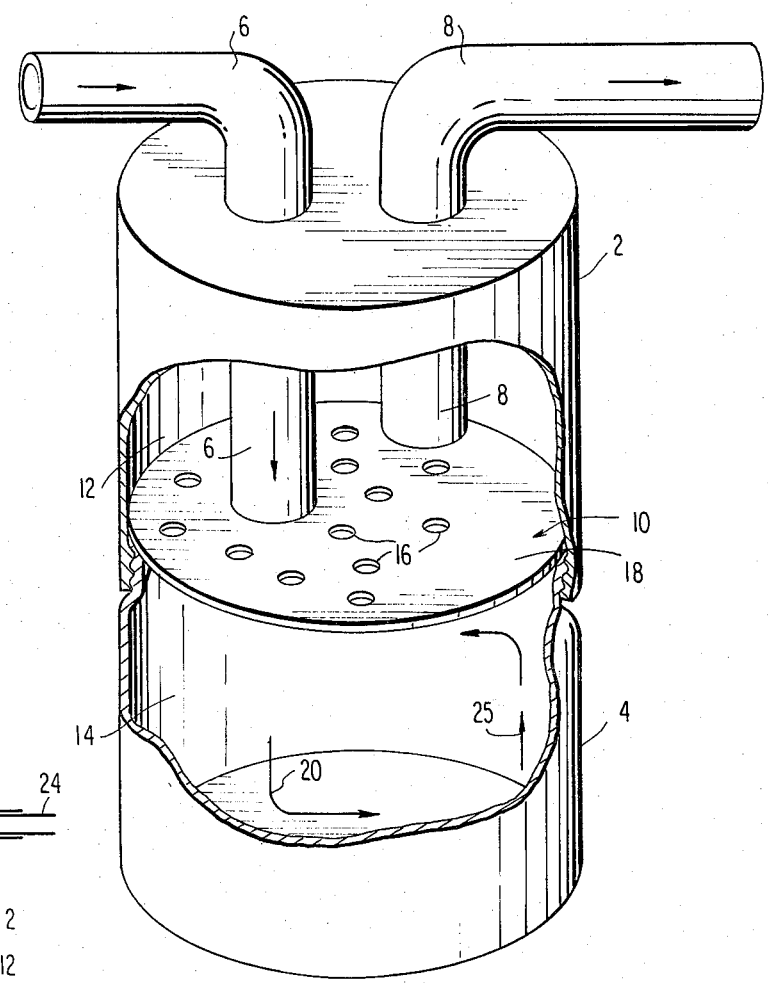
FIG. 1 is a partially broken perspective view of a device constructed according to the invention.
Figure 2:
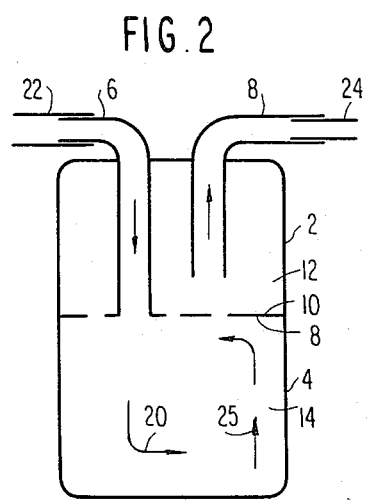
FIG. 2 is a diagrammatic sectional view of the device of FIG. 1, showing its connections to a suction tip and central suction hose.

As seen in FIGS. 1 and 2, the apparatus includes an enclosure formed of an upper section 2 and a lower canister section 4 which are detachably connected and sealed together by mating threads. An inlet conduit 6 and an outlet conduit 8 are connected to and pass in sealed relation through the upper wall of the upper section 2. The upper section 2 in this respect serves as a tall closure for the lower canister section 4.

A baffle 10 is positioned within the enclosure and divides it into an upper chamber 12 and a lower chamber 14. The baffle is affixed to and supported by the lower end of the inlet conduit 6. The conduit 6 opens directly into the lower chamber 14 so that liquid entering the apparatus passes directly from the inlet conduit 6 into the lower chamber 14. The baffle 10 is provided with a plurality of apertures 16, the total area of which is greater than the transverse cross section of the inlet conduit 6. Due to this relationship, any liquid flowing upwardly through the baffle is not significantly accelerated by its movement through the apertures 16. The outlet conduit 8, connected to a vacuum source, has its lower fluid-receiving end located in the upper chamber 12, above the baffle 10.

In FIGS. 1 and 2, it will be noted that the inlet conduit 6 is oriented so that it will introduce its contents axially into one side of the lower chamber. The baffle 10 has an imperforate area 18 located at the opposite side of the chamber from the inlet conduit 6. This disposition will prevent the materials which are moving in the path of arrows 20 and 25 from flowing directly and prematurely into the upper chamber before gravitational settlement has taken place.

As shown in FIG. 2, the horizontal portion of the inlet conduit 6 is telescopically inserted in and connected to the suction tip 22 which, as mentioned above, is manipulated in the patient's mouth for debris removal. The outlet conduit 8 has its horizontal leg telescopically receiving the flexible suction hose 24 which leads first to a debris-trapping device and to a suction pump, both of which, being conventional, are not shown in the drawings.

For convenience, the outer end of the inlet conduit 6 has an outside diameter which is approximately equal to the inside diameter of the conventional suction tip 22. The outer end of the outlet conduit 8 has an inside diameter dimensioned to receive tightly the outside diameter of the suction hose 24. Since the conventional suction tips are dimensioned so that they may telescopically fit over and sealingly engage the suction hose, it follows that the outside diameter of the inlet conduit 6 is approximately equal to but slightly greater than the inside diameter of the outlet conduit 8.

During the operation of the apparatus, the suction pump is activated to create a subatmospheric pressure in the flexible hose 24, the outlet conduit 8 and the upper chamber 12. Negative pressure draws a mixture of debris, air and saliva from the patient's mouth into a lower chamber 14. Since the lower chamber has a substantially greater cross section than the inlet conduit 6, the velocity of the mixture in the lower chamber is substantially reduced, thereby enabling the air to separate from the liquid, and enabling particles of precious metal to settle gravitationally to the bottom of the canister 4. Debris which is less dense remains suspended in the water and flows upwardly through the apertures 16 of baffle 10 and ultimately is drawn into the outlet conduit 8 which carries it to the hose 24, trapping device and vacuum pump. During normal use, it is expected that the liquid level within the device will be approximately at the level of the baffle 10.

Figure 3:
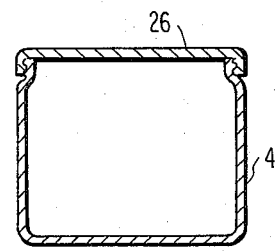
FIG. 3 is a sectional view of a canister which has been capped after being removed from the apparatus of FIG. 1.
Figure 4:
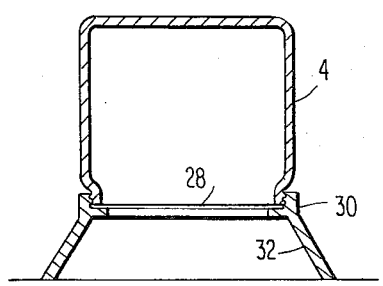
FIG. 4 is a sectional view of a canister which has been removed from the apparatus of FIG. 1, connected to a drainage stand and inverted to drain liquids from the metallic particles.

Preferably, the canister 4 is formed of a material which is sufficiently transparent so that the level of accumulated precious metal particles is visually observable by the doctor and his assistant. After there is sufficient accumulation of precious metal particles, the canister 4 may be removed and replaced by an empty canister. The removed canister may be capped with a closure 26 as shown in FIG. 3, and set aside for further processing. The canister may subsequently be drained as shown in FIG. 4 by covering it with a liquid permeable filter cloth 28, screwing thereto a drainage accessory which includes a threaded open-top rim 30 and three or more spaced apart legs 32. The container is inverted as shown in FIG. 4 so it is supported on legs 32 and the liquid may drain from the metal particles.

When the suction unit is to be used for oral surgery and prophylaxis, the device according to the invention may be removed and the suction tip 22 connected directly to the suction hose 24. Then, the accumulated debris will not contain any precious metal and will be caught in the trapping device and discarded in a conventional manner.

Persons familiar with the field of the invention will realize that the invention may take many forms other than the specific embodiments shown herein. Therefore, it is emphasized that the invention is not limited solely to the disclosed embodiment but is embracing of a variety of modifications to and improvements thereof which fall within the spirit of the following claims.

I claim:

1. Dental apparatus for separating particles of precious metal from a debris-containing mixture received from the mouth of a dental patient, comprising
    an enclosure,
    a baffle and conduit assembly which includes inlet conduit means, outlet conduit means and a baffle means,
    said baffle means being located in said enclosure for dividing the enclosure into an upper chamber and a lower chamber,
    said inlet conduit means being in communication with the lower chamber for introducing into the lower chamber said mixture which contains particles of precious metal, said inlet conduit means having a substantially smaller cross section than said lower chamber so that the mixture in said lower chamber will have a lower velocity than the mixture moving through said inlet conduit means and particles of precious metals may settle gravitationally from the mixture in the lower chamber,
    said baffle means being operable to prevent premature flow of said mixture directly into the upper chamber before gravitational settlement has occurred,
    aperture means extending through the plane of the baffle means for enabling fluids to flow from the lower chamber to the upper chamber, said aperture means having a greater cross sectional area than the inlet conduit means so that fluids flowing from the lower chamber to the upper chamber will have a lower velocity than the mixture flowing through the inlet conduit means into the lower chamber,
    said aperture means having a size which permits debris which is suspended in the mixture and is less dense than the particles of precious metal to flow upwardly through the plane of the baffle to the outlet conduit means,
    said outlet conduit means being in communication with the upper chamber for receiving fluids which have passed from the lower chamber into the upper chamber after particles of precious metal have gravitationally settled therefrom in the lower chamber, means for permitting removal from the apparatus of at least a lower portion of the enclosure means which contains gravitationally settled particles of precious metal.

2. The dental apparatus of claim 1 wherein the inlet conduit means has an outer end portion, and the outlet conduit means has an outer end portion, said outer end portion of the inlet conduit means having an outside diameter which is substantially equal to the inside diameter of the outer end portion of the outlet conduit means.

3. The dental apparatus of claim 2 including a suction tip telescopically fitted over the outer end portion of the inlet conduit means, and a suction hose telescopically received in the outer end portion of the outlet conduit means.

4. The dental apparatus of claim 1 wherein the enclosure means includes a closure, said inlet conduit means and said outlet conduit means being affixed to said closure.

5. The dental apparatus of claim 1 wherein the aperture means includes a plurality of openings in the baffle.

6. The dental apparatus of claim 1 wherein the inlet conduit means is oriented to introduce its contents axially into one side of the lower chamber and, at the opposite side of the chamber, the baffle has an imperforate area to prevent the mixture and particles therein from flowing into the upper chamber.

7. The dental apparatus of claim 1 wherein the enclosure means includes a removable canister which forms the lower chamber.

8. The dental apparatus of claim 1 wherein the inlet conduit means is provided with means for mating with and detachably connecting to a suction tip which is manipulated in a patient's mouth, and the outlet conduit means is provided with means for mating with and detachably connecting to the suction hose of a vacuum pump system.

9. The dental apparatus of claim 1 wherein the baffle means is connected to and supported by the inlet conduit means.

10. The dental apparatus of claim 9 wherein the enclosure means includes a closure, said inlet conduit means and said outlet conduit means being affixed to said closure.

11. The dental apparatus of claim 10 wherein the inlet conduit means is oriented to introduce its contents axially into one side of the lower chamber and, at the opposite side of the chamber, the baffle has an imperforate area to prevent the mixture and particles therein from flowing into the upper chamber.

* * * * *